United States Patent [19]

Toribuchi et al.

[11] Patent Number: 5,420,218
[45] Date of Patent: May 30, 1995

[54] RESINOUS PARTICLES, METHOD FOR PRODUCTION THEREOF, AND USES THEREFOR

[75] Inventors: Hironobu Toribuchi, Takatsuki; Nobuaki Urashima, Suita; Yoshikuni Mori, Takatsuki, all of Japan

[73] Assignee: Nippon Shokubai Co., Ltd., Osaka, Japan

[21] Appl. No.: 77,560

[22] Filed: Jun. 15, 1993

[30] Foreign Application Priority Data

Jun. 16, 1992 [JP] Japan ................................ 4-156295
Jun. 30, 1992 [JP] Japan ................................ 4-172546
May 28, 1993 [JP] Japan ................................ 5-127049

[51] Int. Cl.$^6$ .................................................. C08F 2/18
[52] U.S. Cl. ..................................... 526/214; 526/215; 526/220; 524/260; 524/289
[58] Field of Search ............... 524/259, 260, 247, 302, 524/330, 332, 384, 287, 750; 526/214, 215, 220

[56] References Cited

U.S. PATENT DOCUMENTS

| | | |
|---|---|---|
| 2,744,886 | 5/1956 | Protzman . |
| 4,208,500 | 6/1980 | Matsuo et al. ............... 526/277 |
| 4,833,179 | 5/1989 | Young et al. ............... 526/318.4 |

FOREIGN PATENT DOCUMENTS

| | | |
|---|---|---|
| 50-36262 | 11/1975 | Japan . |
| 51-20989 | 2/1976 | Japan . |
| 52-102391 | 8/1977 | Japan . |
| 55-82125 | 6/1980 | Japan . |
| 57-64522 | 4/1982 | Japan . |
| 57-56507 | 11/1982 | Japan . |
| 58-059202 | 4/1983 | Japan . |
| 59-221304 | 12/1984 | Japan . |
| 59-221305 | 12/1984 | Japan . |
| 59-221306 | 12/1984 | Japan . |
| 59-221307 | 12/1984 | Japan . |
| 60-8302 | 1/1985 | Japan . |
| 61-255353 | 11/1986 | Japan . |
| 62-205108 | 9/1987 | Japan . |
| 2-284905 | 11/1990 | Japan . |
| 3-237105 | 10/1991 | Japan . |
| 4-189837 | 7/1992 | Japan . |

OTHER PUBLICATIONS

European Search Report EP 93 30 4647, 14 Dec. 1993.
Chem. Abstrat. vol. 85, No. 2, p. 6690, Jul. 12, 1976.

*Primary Examiner*—Jeffrey T. Smith
*Attorney, Agent, or Firm*—Omri M. Behr; Matthew J. McDonald

[57] ABSTRACT

A polymeric monomer (A) having as a main component thereof a (meth)acryl type monomer which is subjected to aqueous suspension polymerization in the presence of a compound (B) which is substantially insoluble in water and sparingly soluble in the polymeric monomer (A). The compound (B) has at least one, preferably two or more, structural units, selected from the group consisting of —SH, —S—S—, —COOH, —NO$_2$, and —OH. The use of compound (B), in the suspension polymerization of the (meth)acryl type monomer, represses of the production of by-produced minute particles due to sympathetic emulsion polymerization. The suspension polymerization permits production of meth-)acryl type polymer particles having high heat stability and a small range of particle diameters.

3 Claims, No Drawings

RESINOUS PARTICLES, METHOD FOR PRODUCTION THEREOF, AND USES THEREFOR

BACKGROUND OF THE INVENTION

1. Field of the Invention

This invention relates to resinous particles, a method for the production thereof, and uses therefor. More particularly, in the suspension polymerization of a polymeric monomer having as a main component thereof a (meth)acryl type monomer, this invention relates to technique for repressing the sympathetic occurrence of minute particles due to emulsion polymerization, stabilizing the suspension polymerization, enhancing the yield of the polymerization, and enabling the produced resinous particles to acquire enhanced physical properties. Further, this invention relates to a technique for improving the ability of (meth)acryl type resinous particles to resist heat.

2. Prior Art (Meth)acryl type resinous particles particularly of the class having an average particle diameter in the approximate range of 0.1 to 500 μm are expected to find utility in numerous applications such as for example as an anti-blocking agent for resinous film, an additive for electrostatic image developing toner, a powder coating material and water-dispersion type coating material, an additive for facing panels, an additive for artificial marble, a filler for cosmetic articles, and a filler for a chromatographic column.

Heretofore, as methods for the production of resinous particles, those resorting to mechanical pulverization, to suspension polymerization, and to emulsion polymerization have been known to the art. Of these methods, that which resorts to mechanical pulverization necessitates a huge energy input to pulverize the particles and require many classification steps to enable the resinous particles to be produced with a uniform diameter. Since the minute particles which are obtained by this method are amorphous morphologically, they have room for further improvement in flowability and proofness against flocculation. Although the method which resorts to emulsion polymerization is capable of producing minute particles of uniform diameter, the produced minute particles have a diameter of about 0.1 μm and, therefore, cannot be directly put to such applications as mentioned above. In contrast thereto, the method which resorts to suspension polymerization allows relatively easy production of resinous particles of a desired diameter because it comprises preparing suspended particles of a monomer by mechanical stirring and subjecting the suspended monomer particles to polymerization. It further enjoys such advantages as obviating the necessity for using a solvent and facilitating the reaction control.

It has been known, however, that the suspension polymerization entails secondary formation in the aqueous phase of minute particles due to emulsion polymerization. The secondary reaction lowers the yield of the main polymerization and degrades the stability of this polymerization. Further, since the minute particles formed as described above by emulsion polymerization adhere predominantly to the phase boundary of the particles produced by suspension polymerization and cannot easily be completely removed therefrom, they suffer impairment of the physical properties of the produced resinous particles. Particularly when the resinous particles to be obtained by suspension polymerization are required to have such a small diameter as to be in the approximate range of 0.1 to 500 μm, for example, and since the amount of a dispersion stabilizer to be added to the aqueous phase for ensuring stabilization of the minute suspended particles is large as compared with that for ordinary suspension polymerization, the amount of the polymeric monomer dissolved in the aqueous phase at the step of dispersion and the step of polymerization is increased possibly to the extent of causing the problem of by-production of minute particles due to emulsion polymerization.

As a means for preventing the suspension polymerization from causing emulsion polymerization in the aqueous phase, the addition of an inorganic water-soluble inhibitor to the system has been known to the art. For example, JP-A-55-83,125 discloses the addition of 0.01 to 10% by weight of a water-soluble inhibitor such as ammonium thiocyanate or cupric chloride to water, JP-A-60-8,302 discloses the addition of vanadium pentoxide and/or cupric chloride in combination with a dispersion stabilizer, JP-A-62-205,108 discloses the solution in water of not less than 10 ppm, based on the total amount of vinyl monomers, of such a water-soluble inhibitor as sodium nitrite, potassium nitrite, or cupric chloride, JP-A-2-284,905 discloses suspension polymerization effected by the use of a water-soluble inhibitor such as a nitrite and a polymerization initiator formed of an organic peroxide, and JP-A-3-237,105 discloses suspension polymerization effected in a continuous aqueous phase containing water, a water-miscible organic solvent, and a water-soluble polymerization inhibitor such as sodium nitride or hydroquinone.

Further, as disclosed in JP-A-61-255,353, the technique of adding to an aqueous suspension polymerization system a water-soluble mercaptan compound for the prevention of the sympathetic occurrence of emulsion polymerization has been known to the art. As water-soluble mercaptan compounds, 2-mercaptoethanol, thioglycolic acid, cysteine, glutathione, dimercaprol, 1,4-dithiothreitol, dimercaptosuccinic acid, and 2,3-dimercapto-1-propanesulfonic acid are cited in the specification in support of the disclosure.

JP-A-52-102,391 discloses the addition of about 0.0005 to about 0.02 part by weight of a water-soluble inhibitor selected from among borohydrides represented by the following structural formula (I), alkali metal nitrites, alkaline earth metal nitrites, and ammonium nitrite and about 0.0001 to about 0.005 parts by weight of an oil-soluble inhibitor, oil-soluble and alcohol-soluble nigrosine, respectively based on 100 parts by weight of monomer.

(wherein X is an alkali metal and R, R', and R" independently represent a hydrogen atom, a phenyl group, an alkoxy group, or an alkyl group of one to ten carbon atoms).

In the suspension polymerization of a polymeric monomer having as a main component thereof a (meth)acryl type monomer, even when an inorganic water-soluble inhibitor is added to the reaction system, the effect of the inhibitor in preventing the emulsion polymerization is so weak that the inhibitor must be added in a large amount. Particularly, the conspicuity of this trend grows in proportion as the diameter of minute particles obtained by the suspension polymerization decreases.

When the water-soluble mercaptan compound mentioned above is used for preventing the sympathetic occurrence of emulsion polymerization, this mercaptan compound induces impartation of an offensive odor to the produced resinous particles or the effluent from the polymerization system. This offensive odor is not easily removed by washing.

As regards the use of the borohydride as a water-soluble inhibitor, this compound itself is difficult to handle and, on account of this difficulty, the conditions of the suspension polymerization dictate rigid control.

The various applications cited above are possible outlets for the (meth)acryl type resinous particles. When the resinous particles are used for example, as an anti-blocking agent for resinous film, the characteristic properties which the resinous particles are desirably possess are proximity in the refractive index to the system of resin to which the agent is to be added and ideally the ability to withstand heat.

For example, polyolefin film, is used as a packaging material for wrapping various articles of commerce such as foodstuffs. The film is at a disadvantage in respect that when it is superposed over itself in a multiplicity of layers, the adjoining surfaces of the superposed layers of film fasten cohesively a phenomenon popularly called "blocking," and seriously impairs the operational efficiency of the wrapping. As means conventionally adopted for preventing the polyolefin film from the phenomenon of blocking and imparting an improved slip property to the film, a method which comprises uniformly incorporating minute particles of an inorganic substance such as silica or talc in the film has become very polular. For the purpose of imparting sufficiently the anti-blocking property and slip property to the polyolefin film by the use of such an inorganic substance as mentioned above, however, the inorganic substance must be incorporated in a large amount into the film. Further, when the polyolefin film containing the inorganic substance is stretched., the film is at a disadvantage in that voids occur round the peripheries of the particles of inorganic substance which decreases the film transparency and mechanical strength.

The use of fine powder of polyamide or beads of condensed resin having a triazine ring instead of the inorganic substance mentioned above has been proposed. A method which resorts to the use of the fine powder of polyamide is effective in preventing degradation of transparency. However, it, has the disadvantage in that since it requires this fine powder to be used in a large amount, the fine powder degrades the strength of the film and boosts the cost of production of the film. A method which relies on the use of beads of condensed resin having a triazine ring is unable to adequately prevent the impairment of transparency because of the difference in refractive index between the polyolefin and the condensed resin having a triazine ring. It is further at a disadvantage in that the unaltered volatile substances such as formalin which persist in the condensed resin having a triazine ring give rise to voids during stretching and bring about degradation of the transparency or mechanical strength. Further, at the time that these resinous particles are incorporated in a film, the resinous particles decompose during melting and kneading of the resin for film unless they have sufficient heat stability and the product of this decomposition emits an offensive odor and induces the occurrence of voids possibly to the extent of polluting the environment and impairing mechanical and optical properties of the produced film. Thus, the resinous particles should desirably have a further improved heat stability.

SUMMARY OF THE INVENTION

An object of this invention, therefore, is to provide resinous particles of improved quality, a method for the production thereof, and various uses for the resinous particles. Another object of this invention is to provide resinous particles of excellent physical properties obtained by the suspension polymerization of a polymeric monomer having as a main component thereof a (meth)acryl type monomer and a method for the production thereof. Still another object of this invention is to provide suspension polymerized resinous particles which only sparingly from suffer the inclusion therein of minute particles sympathetically by-produced by emulsion polymerization and a method for the production thereof. Further, in the suspension polymerization of a polymeric monomer having as a main component thereof a (meth)acryl type monomer, this invention has as yet another object thereof the provision of a method for the production of resinous particles which represses the possible occurrence at the phase boundary of the suspended particles such fine particles as sympathetically by-produced by emulsion polymerization and promotes the improvement of stability of polymerization, the enhancing the yield of production, and the enhancement of physical properties of the produced :particles. A further object of this invention is to provide (meth)acryl type resinous particles excelling particularly in heat stability, a method for the production thereof, and uses therefor.

The objects described above are accomplished by a method for the production of resinous particles which is characterized by subjecting a polymeric monomer having a main component thereof a (meth)acryl type monomer (A) to aqueous suspension polymerization in the presence of a compound (B) substantially insoluble in water and sparingly soluble in the polymeric monomer (A) mentioned above, compound (B) having at least one structural unit selected from the group consisting of —SH, —S—S—, —COOH, —NO$_2$, and —OH. Compound (B) is desired to have two or more structual units selected from the above mentioned group. The amount of the compound (B) to be added is preferably in the range of 20 to 0.0001% by weight, based on the amount of the polymeric monomer (A). With respect to the suspension polymerization, it is permitted to incorporate into the polymerization system any additives such as plasticizer, polymerization stabilizer, coloring agent, fluorescent whiting agent, magnetic powder, ultraviolet absorbent, antistatic agent, and flame retardant.

The objects described above are further accomplished by resinous particles of a (meth)acryl type polymer which are characterized in that after 40 minutes' heating at 270° C. in the air, the organic component thereof is decomposed at a ratio of not more than 60% by weight.

The resinous particles preferably have an average particle diameter in the range of 0.1 to 500 μm. The resinous particles, in the state not incorporating therein a coloring agent, may exhibit a refractive index in the approximate range of 1.45 to 1.55. The resinous particles, depending on their intended use to be selected, may assume the state incorporating therein various additives such as selected from among those cited above.

This invention is further directed to a polyolefin type polymer composition comprising the resinous particles mentioned above and a polyolefinic resin. The proportion of the resinous particles to the polyolefinic resin is preferably in the approximate range of 0.001 to 40% by weight.

This invention is also directed to a polyolefin type polymer film formed by incorporating the resinous particles mentioned above into a polyolefinic resin sheet. The proportion of resinous particles to polyolefin is preferably in the approximate range of 0.001 to 5% by weight.

This invention further is directed to a cosmetic article formed by having the resinous particles mentioned above incorporated as a filler.

Further, this invention is directed to a coating composition formed by incorporating the resinous particles mentioned above in a binder.

This invention, by effecting the aqueous suspension polymerization of the polymeric monomer (A) having as a main component thereof, a (meth)acryl type monomer in the presence of a compound (B) having the above mentioned specific structual unit and being substantially insoluble in water and sparingly soluble in the polymeric monomer (A), can repress the possible sympathetic occurrence of emulsion polymerization of part of the polymeric monomer (A) which is dissolved in the aqueous phase and promote enhancement of the stability of polymerization, the yield of production, and the physical properties, especially heat stability and uniformity of the particle diameters, of the produced particles.

DETAILED DESCRIPTION OF THE INVENTION

We, inventors have made a diligent study in search of a method for repressing the sympathetic occurrence of emulsion polymerization in the aqueous suspension polymerization of a polymeric monomer having as a main component thereof a (meth)acryl type monomer with attention focussed on the fact that this emulsion polymerization takes place predominantly on the phase boundary of the suspended particles. As a result, we have acquired a knowledge that when the compound (B) which has the aforementioned specific structual unit and which is substantially insoluble in water and sparingly soluble in the polymeric monomer mentioned above is used, this compound (B) can be efficiently distributed on the phase boundary of the suspended particles in the aqueous polymerization and can effectively repress the emulsion polymerization which would otherwise occur on the phase boundary of the suspended particles.

It has also been found that the resinous particles of (meth)acryl type polymer which are obtained by the suspension polymerization carried out in the presence of this compound (B) preeminently excels in heat stability as compared with the conventional resinous particles. The precise reason for this good result remains yet to be determined. We did not anticipate that the compound (B) would have an effect other than the effect of repressing the emulsion polymerization at the phase boundary of the suspended monomer particles. It was beyond our expectation for compound (B) to have the effect of improving the heat stability of the suspension polymerized resinous particles Now, this invention will be described in detail below with reference to embodiments thereof.

The polymeric monomer (A) to be used in this invention has as a main component thereof a (meth)acryl type monomer. To be more specific, it preferably contains 50 to 100% by weight, more preferably 60 to 100% by weight, of the (meth)acryl type monomer therein. If the proportion of (meth)acryl type monomer to polymeric monomer (A) is extremely small, the effect which compound (B) has in inhibiting the emulsion polymerization as specifically described hereinbelow can be expected to be small. Therefore, it is preferable that the SP (solution parameter) value of the polymeric monomer (A) should be not more than 9.0.

The (meth)acryl type monomers which are effectively usable herein include, for example, acrylic acid, acrylic esters such as methyl acrylate, -ethyl acrylate, n-butyl acrylate, isobutyl acrylate, dodecyl acrylate, stearyl acrylate, 2-ethylhexyl acrylate, tetrahydrofufuryl acrylate, methacrylic acid, methyl methacrylate, ethyl methacrylate, propyl methacrylate, n-butyl methacrylate, isobutyl methacrylate, n-octyl methacrylate, dodecyl methacrylate, 2-thyl-hexyl methacrylate, and stearyl methacrylate. Of course, these are not exclusive examples. It is also permissible to use two or more of these (meth)acryl type monomers in a combined state.

For the purpose of obtaining resinous particles having an intermolecular cross-linked structure, it is allowable to copolymerize a (meth)acryl type monomer having a plurality of polymeric double bond groups in the molecular unit thereof with the aforementioned (meth)acryl type monomer. The cross-linking (meth)acryl type monomers which answer the description given above include, for example, trimethylol propane triacrylate, ethylene glycol dimethacrylate, diethylene glycol dimethacrylate, triethylene glycol dimethacrylate, decaethylene glycol dimethacrylate, pentadecaethylene glycol dimethacrylate, pentacontahectaethylene glycol dimethacrylate, 1,3-butylene dimethacrylate, allyl methacrylate, trimethylol propane trimethacrylate, pentaerythritol tetramethacrylate, and diethylene glycol dimethacrylate. It is allowable to use a plurality of these (meth)acryl type monomers in a combined state. It is permissible to use in the copolymerization as a cross-linking agent an aromatic divinyl compound such as divinyl benzene, divinyl naphthalene, or a derivative thereof, a cross-linking agent such as N,N-divinyl aniline, divinyl ether, divinyl sulfide, or divinyl sulfonic acid, an unsaturated polyester such as polybutadiene or polyisoprene, and any of the reactive polymers disclosed in JP-B-57-56,507, JP-A-59-221,304, JP-A-59-221,305, JP-A-59-221,306and JP-A-59,221,307 in amounts not large enough to disrupt the specific proportion of the (meth)acryl type monomer in the polymeric monomer (A) mentioned above.

The other monomer which may be contained in the polymeric monomer (A) used in this: invention is only required to be capable of copolymerizing with the (meth)acryl type monomer mentioned above. The monomers which are thus usable effectively herein include, for example, styrene type monomers such as styrene, o-methyl styrene, m-methyl styrene, p-methyl styrene, α-methyl styrene, p-methoxy styrene, p-tert-butyl styrene, p-phenyl styrene, o-chloro styrene, m-chloro styrene, and p-chloro styrene, and ethylene, propylene, butylene, vinyl chloride, vinyl acetate, acrylonitrile, acryl amide, methacryl amide, and N-vinyl pyrrolidone.

The method of this invention for the production of resinous particles, in the aqueous suspension polymerization of the polymeric monomer (A) of the kind described above, requires the addition to the suspension polymerization system of compound (B) which is substantially insoluble in water and sparingly soluble in the polymeric monomer (A) mentioned above.

Since the compound (B) used as described above in this invention is substantially insoluble in water and sparingly soluble in the polymeric monomer (A), the compound (B) in the suspension polymerization system is forced, by the action of a dispersion stabilizer such as a surfactant which is added to the suspension polymerization system as described specifically hereinbelow to be present at the phase boundary of the suspended particles and thereby accomplish effective repression of the emulsion polymerization which would otherwise occur at the phase boundary of the suspended particles. If the solubility of compound (B) in water is unduly high, the compound (B) during the suspension polymerization is forced to pass into the aqueous phase lying contiguously to the phase boundary and consequently is unable to affect the emulsion polymerization. If the solubility of compound (B) in the polymeric monomer (A) is unduly high, it is liable to induce chain transfer in the suspended particles (monomer) and prevent the degree of polymerization of the produced resinous particles from increasing.

The solubility of the compound (B) in water, under the conditions of 25° C. ±5° C. and 760 Torrs, is preferably in the approximate range of 0 to 1% by weight, more preferably 0 to 0.1% by weight. The solubility of the compound (B) the polymeric monomer (A), under the conditions of 25° C. ±5° C. and 760 Torrs, is preferably in the approximately range of 0 to 50% by weight, more preferably 0. 01 to 20% by weight, and most preferably 0.01 to 10% by weight.

The compound (B) which satisfies the conditions regarding the solubility in water and in the polymeric monomer (A) described above has at least one structural unit selected from the group consisting of —SH, —S—S—, —COOH, —NO₂, and —OH.

As concrete examples of the compound having —SH group(s), thiocresol, thiophenol, methyl thioglycolate, ethyl thioglycolate, butyl thioglycolate, 2-ethylhexyl thioglycolate, trimethylol propane trithioglycolate, xylene dithiol, and 2-mercaptonaphthalene are cited. As concrete examples of the compound having —S—S— group(s), diallyl disulfide and dioctyl dithiopropionate are cited. As concrete examples of the compound having —COOH group(s), cinnamic acid, benzoic acid, chlorobenzoic acid, phthalic acid, and isophthalic acid are cited. As concrete examples of the compound having —NO₂ group(s), nitrobenzene, nitrotoluene, nitroxylene, nitronaphthalene, and nitroaniline are cited. As concrete examples of the compound having —OH group(s), amino cresol, amino naphthol, m-cresol, oxyanthracene, oxyanthraquinone, oxanthrone, 3-oxy-9-anthrone, oxynaphthoquinone, dioxyanthracene, dioxyanthraquinone, 1,5-dioxy-naphthalene, 1,8-dioxynaphthalene, 2,6-dioxy-naphthalene, 3,5-dimethyl phenol, and naphthol are cited.

Further, the compound (B) to be used in this invention proves to be particularly preferred when it has two or more structural units selected from the group consisting of —SH, —S—S—, —COOH, —NO₂, and —OH. As concrete examples of the compound answering this description, salicylic acid, thiosalicylic acid, dithiosalicylic acid, nitrobenzoic acid, 3,4-dinitrobenzoic acid, and nitrophenol are cited.

In the aqueous suspension polymerization contemplated by this invention, although the amount of the compound (B) to be added is affected as by, for example, the type of compound (B) used and the composition of the polymeric monomer (A), it is in the approximate range of 20 to 0.0001% by weight, preferably 10 to 0,001% by weight, and more preferably 5 to 0.01% by weight, based on the amount of the polymeric monomer (A) mentioned above. If the amount of compound (B) to be added is less than 0.0001% by weight, the effect of this agent in inhibiting emulsion polymerization is too small to prevent the occurrence of minute particles. Conversely, if the amount exceeds 20% by weight, this agent is liable to induce chain transfer within the suspended particles (monomer) and prevent the degree of polymerization of the produced resinous particles from increasing.

The method for adding this compound (B) to the copolymerization system is not particularly specified. For example, a method which comprises adding the compound (B) into the polymeric monomer (A), a method which comprises adding the compound (B) to the aqueous phase, and the method which comprises dissolving the compound (B) in a solvent such as methanol and dispersing the resultant solution in the aqueous phase, are available.

The method of this invention for the production of resinous particles resides in subjecting the polymeric monomer (A) having as a main component such a (meth)acrylate type monomer as described above to aqueous suspension polymerization in the presence of the compound (B) as described above. The polymerization temperature suitably is in the approximate range of 10° to 90° C., preferably 30° to 80° C. This suspension polymerization is preferably carried out either after regulation of diameter of the suspended particles of polymeric monomer (A) has been completed or while the regulation is in process. Preferably, it is carried out after regulation of the particle diameter. This regulation of the particle diameter is effected by dispersing the prescribed reactant components in an aqueous medium and stirring the resultant suspension using a T.K. homomixer. It may otherwise be effected by passing the reactant components once to several times through such a high-speed stirring device such as a line mixer (Ebara Milder of Ebara Mgf. Co. Ltd. for example).

The suspension polymerization system may incorporate therein a dispersion stabilizer with a view to stabilizing the suspended particles. The dispersion stabilizers which are effectively used herein include, for example, water-soluble macromolecular compounds such as polyvinyl alcohol, gelatin, tragacanth, starch, methyl cellulose, carboxy methyl cellulose, hydroxy ethyl cellulose, sodium polyacrylate, and sodium polymethacrylate, anionic surfactants, cationic surfactants, ampholytic surfactants, nonionic surfactants, and alginates, zein, casein, barium sulfate, calcium sulfate, barium carbonate, magnesium carbonate, calcium phosphate, talc, clay, diatomaceous earth, bentonite, titanium hydroxide, thorium hydroxide, and powdered metal oxides.

As the anionic surfactants, fatty oils such as, for example, sodium oleate and potassium salt of castor oil, alkyl sulfates such as sodium lauryl sulfate and ammonium lauryl sulfate, alkyl benzen sulfonates such as dodecyl benzen sulfonate, alkyl naphthalene sulfonates, alkane sulfonates, dialkylsulfosuccinates, alkyl phosphoric esters, condensetes of naphtalene sulfonic acid with formalin, polyoxyethylene alkylphenylether sulfates, and polyoxyethylene alkyl sulfates are cited. The nonionic surfactant includes polyoxyethylene alkyl ethers, polyoxyethylene alkylphenyl ethers, polyoxyethylene fatty esters, sorbitan fatty esters, polyoxysorbitan fatty esters, polyoxyethylene alkylamines, glycerol fatty esters, oxyethylene—oxypropylene block polymers. The cationic surfactant includes, for example, alkylamine salts such as lauryl amine acetate and stearyl amine acetetes, and quaternary ammonium salts such as lauryl trimethylammonium chloride, for example. The ampholytic surfactant includes lauryl dimetyl amine oxide.

The dispersion stabilizer must be used with the composition thereof and the amount of use thereof suitably adjusted so that the produced resinous particles will acquire a prescribed diameter in the range of 0.1 to 500 μm, desirably 0.5 to 100 μm. Specifically, the amount of the dispersion stabilizer used is in the range of 0.01 to 29% by weight, preferably 0.1 to 10% by weight, based on the amount of the polymeric monomer (A).

As the polymerization initiator to be used for the polymerization in this invention, any of the oil-soluble peroxide type and azo type initiators which are generally used for suspension polymerization can be adopted. The initiators which are effectively used herein include, for example, peroxide type initiators such as benzoyl peroxide, lauroyl peroxide, octanoyl peroxide, benzoyl orthochloroperoxide, benzoyl orthomethoxyperoxide, methylethyl ketone peroxide, diisopropyl peroxy dicarbonate, cumene hydroperoxide, cyclohexanone peroxide, t-butyl hydroperoxide, and diisopropyl benzene hydro-peroxide, and azo type initiators such as 2,2'-azo-bis-isobutyronitrile, 2,2'-azo-bis(2,4-dimethyl valeronitrile), 2,2'-azo-bis-(2,3dimethyl butyronitrile), 2,2'-azo-bis(2-dimethyl butyronitrile), 2,2'-azo-bis(2,3,3-trimethyl butyronitrile), 2,2'-azo-bis(2-isopropyl butyronitrile), 1,1'-azo-bis(cyclohexane-1-carbonitrile), 2,2'-azo-bis(4-methoxy-2,4-dimethyl valeronitrile), 2-(carbamoyl-azo) isobutyronitrile, 4,4'-azo-bis(4-cyanovaleric acid), and dimethyl-2,2'-azo-bis-isobutyrate. The polymerization initiator is preferably used in an amount in the range of 0.01 to 20% by weight, more preferably 0.1 to 10% by weight, based on the amount of the polymeric monomer (A).

In preparation for the suspension polymerization, the polymeric monomer (A) or the aqueous phase, when necessary, may have such a coloring agent as a pigment or dye or other additive incorporated therein or added thereto.

The pigments which are usable effectively used herein include, for example, inorganic pigments such as white lead, minium, chrome yellow, carbon black, ultramarine, zinc oxide, cobalt oxide, titanium dioxide, iron oxide, silica, titanium yellow, and titanium black and organic pigments such as isoindolinone, quinacridone, dioxane violet, phthalocyanine blue, perinone pigment, perylene pigment, insoluble azo pigments, soluble azo pigments, and dye lake.

The dyes which are effectively used herein include, for example, nitroso dye, nitro dye, azo dye, stilbene azo dye, diphenyl methane dye, triphenyl methane dye, xanthene dye, acridine dye, quinoline dye, methine dye, polymethine dye, thiazole dye, indamine dye, indophenol dye, azine dye, oxazine dye, thiazine dye, and sulfide dye.

The other additives which are effectively used herein include, for example, plasticizer, polymerization stabilizer, fluorescent whiting agent, magnetic powder, ultraviolet absorbent, antistatic agent, and flame retardant. The magnetic powder may be colored and can be used as coloring agent either independently or in combination with other coloring agent.

The coloring agent and other additive mentioned above may have been given a surface treatment by svarious method for the purpose of having the dispersibility thereof in the polymeric monomer (A) improved. The methods which are effectively used for the surface treatment include, for example, a method which effects the treatment with a long-chain hydrocarbon such as stearic acid or oleic acid, a method which effects the treatment with a polymeric monomer having a polar group such as an acrylic acid or a methacrylic acid, a method which effects the treatment with a polyhydric alcohol such as a trimethylol propane, a method which effects the treatment with an amine such as triethanol amine, a method which effects the treatment with various coupling agent, and a method which comprises causing the coloring agent or other additive to react at a temperature in the range of 20° to 350° C. with a polymer having a reactive group such as aziridine group, oxazoline group, N-hydroxyalkylamide group, epoxy group, thioepoxy group, isocyanate group, vinyl group, silicon type hydrolyzing group, or amino group which can react with the functional group on the surface of the coloring agent or other additive mentioned above thereby grafting the polymer on the surface of the coloring agent or other additive.

The resinous particles which are obtained by the method of production of this invention performed as described above avoid by-production of minute particles due to sympathetic emulsion polymerization and have an extremely narrow particle diameter distribution having an average diameter in the approximate range of 0.1 to 500 μm, preferably 0.5 to 100 μm, and more preferably 0.5 to 30 μm because the emulsion polymerization which otherwise occurs sympathetically at the phase boundary of the suspended particles and the aqueous phase during the suspension polymerization is repressed by the action of the radical sequestrate (B) mentioned above. Further, the resinous particles which are obtained by the method of production of this invention acquire very high heat stability. Typically, this heat stability is such that the ratio of decomposition of the resinous particles caused after 40 minutes' standing at 270° C. in the air is not more than 60% by weight, preferably not more than 40% by weight, and more preferably not more than 30% by weight.

The ratio .of the decomposition of the organic component attained as a consequence of standing at the prescribed temperature as stated herein is the magnitude to be obtained by heating a given sample at a heating rate of 40° C./minute from room temperature to 200° C., then continuing this heating at a gradually decreased heating rateso adjusted that the time required for the temperature to rise from room temperature to 270° C. totals 20 minutes, allowing the sample which has reached 270° C. to stand at that temperature for 40 minutes, and weighing the sample at the end of the standing thereby finding the decrease in the weight of the sample by heating. The sample size of resinous particles for the test is about 20 mg and the test is carried out under the condition of supplying clear air to the site of the test at a rate of about 40 ml/min. The term "organic component" as used herein refers exclusively to the polymer component originating in the polymeric monomer and does not contemplate the organic coloring agent and other components which are optionally added to the resinous particles.

Since the resinous particles obtained by the method of production of this invention or the liquid having such resinous particles suspended therein can be ideally used in various applications because the resinous particles excel in heat stability and have outstanding properties such as a very narrow particle diameter distribution as described above.

For example, the resinous particles contemplated by this invention are ideally used as an anti-blocking agent for films, particularly as an anti-blocking agent for polyolefinic films.

The polyolefin type polymer composition contemplated by this invention is a product obtained by incorporating the resinous particles mentioned above in a polyolefin. This polyolefin type polymer composition per se can be used for obtaining a polyolefin type polymer film by forming in the shape of a film the composition Alternatively, the polymer composition may be used in a diluted form with an additional polyolefin. The polyolefin type polymer film contemplated by this invention is a product obtained by incorporating the aforementioned resinous particles in a polyolefin. The polyolefin type polymer film which is produced by incorporating the resinous particles therein as described above is outstanding in some properties such as anti-blocking property, slip property, transparency, and mechanical strength.

When the aforementioned resinous particles are incorporated in the polyolefin, since the resinous particles have a sufficiently high heat stability as described above, the possibility that the component forming the resinous particles will decompose with the evolution of a volatile component while the resinous particles are being melted and kneaded during the formation of film and that the volatile component will give rise to voids, the possibility that the produced film will consequently suffer from degradation of optical and mechanical properties thereof, and the possibility that the offensive odor emanating from the volatile component will cause environmental pollution are all nil.

The resinous particles contemplated by this invention, while in a state not incorporating therein a coloring agent, exhibit a refractive index in the range of 1.45 to 1.55, a value which closely approximates the refractive index of the polyolefin. Therefore, when the resinous particles of this invention are used as an anti-blocking agent in the polyolefin, there is no possibility of degrading the transparency of the produced film. Generally, when the resinous particles have incorporated therein a certain additive for the purpose of improving the heat stability, there is a strong possibility of causing their refractive index to deviate from the range specified above. The resinous particles conforming to this invention have no use for such an additive as mentioned above and, therefore, have a desirable refractive index. In order for the resinous particles to be effectively incorporated as an anti-blocking agent in the polyolefin, they preferably have a refractive index in the range of 1.47 to 1.53, more preferably 1.48 to 1.52.

The resinous particles of this invention, for the purpose of serving effectively as an anti-blocking agent, preferably have a cross-linked structure and exhibit relatively low hardness of not more than 5H, preferably not more than 4H, in terms of pencil hardness so that the film produced using the resinous particles will produce ideal resistance to scratching.

The amount of resinous particles to be incorporated in the polyolefin type polymer composition of this invention is suitably in the approximate range of 0.001 to 40% by weight, preferably 0.005 to 35% by weight, based on the amount of the polyolefin. The amount of the resinous particles to be incorporated in the aforementioned polyolefin type polymer film is suitably in the approximate range of 0.001 to 5% by weight, preferably 0.005 to 3% by weight, and more preferably 0.01 to 2% by weight, based on the amount of the polyolefin. The polyolefin type polymer film of this invention is able to acquire ideal anti-blocking properies and slip properties by the incorporation of such a relatively small amount of resinous particles as specified above. If the amount of resinous particles to be incorporated as described above is less than 0.001% by weight, the produced film does not easily acquire as high anti-blocking properties or slip properties as expected. Conversely, if this amount exceeds 5% by weight, the produced film suffers from a degradation of strength.

In order for the resinous particles of this invention to be effectively used as an anti-blocking agent as described above, they are preferably to have an average particle diameter in the range of 0.1 to 30 $\mu$m, more preferably 0.3 to 25 $\mu$m, and most preferably 0.5 to 20 $\mu$m. If the average particle diameter is less than 0.1 $\mu$m, since the effect of the resinous particles in regard to improving the anti-blocking property and the slip property of the produced film is insufficient, the resinous particles must be used in an amount which is possibly so large as to impair the mechanical property of the film. Conversely, if the average particle diameter exceeds 30 $\mu$m, the produced film is liable to shed the resinous particles possibly to the extent of degrading the mechanical strength of the film.

The polyolefins which are effectively used in the production of the polyolefin type polymer composition and the polyolefin type polymer film both contemplated by this invention include, for example, homopolymers, random copolymers, and block copolymers of such $\alpha$-olefins as ethylene, propylene and butylene, and mixtures thereof. Among other polyolefin type polymers cited above, polymers having as a main component thereof ethylene and/or propylene are preferably used. It is permissible for the polyolefin type polymer composition or the polyolefin type polymer film of this invention to incorporate therein various additives in amounts not large enough to produce any adverse influence on the effect of the incorporation of the resinous particles. The additives which are effectively used herein include, for example, various stabilizers such as antioxidant and ultraviolet absorbent, flame retardant, antistatic agent, coloring agent, and inorganic filler. Such a conventional anti-blocking agent as silica may be additionally incorporated.

The dispersion of the resinous particles in a polyolefin can be attained by the use of any of the well-known mixing devices such as, for example, a ribbon blender, a Banbury mixer, a super mixer, and an extruder. As means for adjusting the content of such resinous particles in the polyolefin type polymer film, a method which comprises preparing a master batch containing the resinous particles in a high concentration by the technique described above, diluting this master batch with an additional polyolefinic resin, and forming the product of dilution in the shape of film proves to be preferred in the sense that the resinous particles are dispersed very uniformly.

The polyolefin type polymer film of this invention can be obtained by any of various well-known methods such as, for example, inflation molding, calender molding, and T-die molding methods. It can be produced in the form of a single-layer film, uniform in composition throughout the entire volume thereof or a laminate film having films of identical or non-identical types superposed. As a means for obtaining a laminate film, a method which comprises forming component films independently of each other and then superposing these component films by the dry laminating technique or the heat laminating technique, a method which comprises preparatorily forming a film and then extrusion laminating the resin onto the film, and a method which comprises simultaneously forming a laminate film by the multi-layer coextrusion technique may be cited as examples.

The film which has been obtained by such a method as cited above can be subjected further to a stretching treatment to give rise to a stretched polyolefinic film. At least one surface of the polyolefin type polymer film, when necessary, may be subjected to a corona discharge treatment. The corona discharge treatment possibly enhances the film in such properties as its anti-blocking property and slip property.

Regarding another embodiment, the resinous particles of this invention, particularly those of the type containing titanium dioxide or an ultraviolet absorbent, are used favorably for cosmetic articles because they exhibit ideal ultraviolet absorbing property and weatherability. As concrete examples of the cosmetic articles, foundations such as powder foundation, creamy foundation, O/W or W/O type milky foundation, and O/W or W/O type oil cake foundation, creamy and milky lotions such as O/W or W/O type cream and O/W or W/O type milky lotion, suspension type cosmetics having particles dispersed in water, aqueous alcohol, and oil, and lip cream, anti-sunburn oil, cheek rouge, eye shadow, and mascara may be cited.

The cosmetic articles contemplated by this invention are obtained by mixing the resinous particles mentioned above with conventional cosmetic grade bases in the manner common in the art. The cosmetic grade bases which are favorably used for this purpose include, for example, silicone oils such as dimethyl polysiloxane, methyl polysiloxane, dimethyl cyclopolysiloxane, and methyl hydrogen polysiloxane, hydrocarbons such as solid and liquid paraffins, crystal oil, ceresin, ozokerite, and montan wax, vegetable and animal oils and waxes such as olive, earth wax, carnauba wax, lanolin, and whale wax, fatty acids and esters thereof such as stearic acid, palmitic acid, oleic acid, glycerin monostearates, isopropyl myristates, isopropyl stearates, and butyl stearates, and alcohols such as ethyl alcohol, isopropyl alcohol, cetyl alcohol, stearyl alcohol, palmityl alcohol, and hexyldodecyl alcohol. Such polyhydric alcohols as glycol, glycerin, and sorbitol which have an ability to retain moisture are similarly usable. The powders which are effectively used as bases include, for example, loading pigments such as mica, talc, sericite, kaolin, and nylon powder, inorganic pigments such as titanium dioxide, zinc white, iron oxide, and pearl, and organic pigments such as red pigment 202, red pigment 226, yellow pigment 4, and aluminum lake. Further, the powders obtained by subjecting the powders just mentioned to the known hydrophobic surface treatments using silicon, metallic soap, N-acyl glutamic acid are also usable. The cosmetic articles of this invention are allowed to incorporate further therein such additives as water, surfactant, tackifier, antiseptic, and antioxidant which are in popular use in cosmetic articles.

The amount of the resinous particles of this invention to be used in cosmetic articles, though variable with the type of cosmetic article, generally falls in the range of 0.1 to 70% by weight, preferably 0.5 to 50% by weight, and more preferably 1 to 25% by weight.

A coating composition constitutes itself another use found for the resinous particles of the present invention. As concrete examples of the coating composition, coating agents for imparting anti-blocking properties and slip properties to outer film or surface of various coats may be cited. The binders which are effectively usable for such coating compositions include thermo-plastic resins, thermosetting resins, and reactive resins which are capable of forming a coat on various substrates when applied thereto. These resins are used either singly or in the form of a combination of two or more members, depending on the purpose of use.

The thermoplastic resin, used advantageously, preferably has an average molecular weight in the approximate range of 1,000 to 1,000,000. The concrete examples of the thermoplastic resin which answers this description include vinyl chloride type resins such as polyvinyl chloride and vinyl chloride-vinylidene chloride copolymer, vinyl ester type resins such as polyvinyl acetate, vinyl acetate-ethylene copolymer, and vinyl acetate-methyl methacrylate copolymer (meth)acrylic ester type resins such as (meth)acrylic ester (co)-polymer, (meth)acrylic ester-acrylonitrile copolymer, and (meth)acrylic ester-styrene copolymer, styrene type resins such as styrene-butadiene-acrylonitrile copolymer, polyamide type resins such as poly($\epsilon$-caprolactam) and the condensate of adipic acid with hexamethylene diamine, polyester type resins such as the condensate of terephthalic acid with ethylene glycol and the condensate of adipic acid with ethylene glycol, polyolefin type resins such as polyethylene, chlorinated polypropylene, carboxyl-modified polyethylene, polyisobutylene, and polybutadiene, cellulose derivatives such as cellulose acetate, cellulose propionate, and nitrocellulose, and butyral resin. When these resins are available in the market, they may be used in their unmodified form. Otherwise, they may be synthesized by pertinent methods heretofore known in the art.

The thermosetting resin or the reactive resin is capable of forming a cross-linked structure due to an addition reaction, a condensation reaction or the like by being heated, exposed to an active energy ray, dried, or treated otherwise during or after the formation of a coating. As concrete examples of the thermo-setting resin or reactive resin which answers this description, phenol type resins such as novolac resin and resol resin, amino type resins such as urea resin, melamine resin, and benzoguanine resin, various alkyd resins, unsaturated polyester resins, curing acryl type resin, urethane-modified resins such as isocyanate group-containing polyesters and isocyanate group-containing poly-ethers, polyamine type resins, and epoxy resin may be cited.

The binders mentioned above are selected in accordance with the ability to adhere fast to and wet a substrate to be coated and such properties as hardness, flexibility, resistance to chemicals, resistance to pollution, and weatherability which are expected of a coating. They are used either singly or in the form of a combination of two or more members in due consideration of the purposes for which the relevant coating compositions are used.

The coating composition of the present invention containing resinous particles can be obtained by a method of dispersing the resinous particles in a variable binder. The ratio of the amount of the binder used in the coating composition to the amount of resinous particles contained in the coating composition is not particularly specified. For the purpose of enabling the coating composition to sufficiently produce the characteristic quality thereof and, at the same time, retain the quality as a coating intact, the resinous particles may be used in an amount in the range of 0.01 to 300 parts by weight, preferably 0.05 to 200 parts by weight, based on 100 parts by weight of the binder. The resin particle-containing coating composition of this invention, when necessary, may incorporate therein in addition to the components mentioned above the well-known additives intended for a coating composition in amounts not large enough to jeopardize the effect of the resinous particles. The additives which are effectively usable for the additional incorporation include, for example, metallic soap, dispersion aids such as surfactant, film-forming auxiliary, anti-static agent, defoaming agent, silica, talc, calcium carbonate, and inorganic pigments such as titanium dioxide.

Besides the uses mentioned above, the resinous particles of this invention can be ideally used, for example, as an additive for an electrostatic developing toner, an additive for a facing panel, an additive for artificial marble, a filler for a chromatographic column, a gap-adjusting agent for a liquid crystal display panel, a display powder for a coal tar counter, and a carrier for an immunodiagnostic medicine.

EXAMPLES

Now, this invention will be described more specifically below with reference to the working examples. These examples will not limit this invention in any respect. Wherever the expression "parts" is used in the following working examples, it shall be construed invariably as referring to parts by weight.

Example 1

A flask provided with a stirrer, an inert gas inlet tube, a reflux condenser, and a thermometer was charged with 900 parts of deionized water having dissolved therein 0.5 part of polyoxy-ethylene alkylsulfoammonium (produced by Dai-ichi Kogyo Seiyaku Co., Ltd. and marketed under trademark designation of "Hitenol N-08"). To the flask, a mixture prepared in advance of 90 parts of methyl methacrylate, 10 parts of trimethylol propane trimethacrylate, 1 part of azoisobutyronitrile, and 1 part of 3,4-dinitrobenzoic acid was added, then the resultant mixture was stirred for five minutes at a rate of 8000 r.p.m. with a T. K. Homogenizer (a proprietary product of Tokushu Kika Kogyo K.K.) to give rise to a homogeneous suspension.

The solubility of 3,4-dinitrobenzoic acid to water was 0.29% under the conditions of 23° C. and 760 Torrs and the solubility thereof to the polymeric monomer used was 16%.

Then, the suspension was blown with a forced current of nitrogen gas and, at the same time, heated to 75° C. Then, it was continuously stirred at this temperature for five hours to effect suspension polymerization and thereafter cooled. The suspension was filtered and then dried to obtain resinous particles (1). The filtrate obtained at this time was found to contain 1.48 g of a nonvolatile component (fine particles of emulsion polymerization).

By measurement with a Coulter Counter (aperture 100 μm), the resinous particles (1) were found to have an average particle diameter of 3.47 μm with a standard deviation of 1.4 μm. The resinous particles (1) were colorless and odorless.

The ratio of decomposition of the organic component of the resinous particles (1) after 40 minutes' standing in the air at 270° C., determined by the use of a thermogravimetric analyzer (produced by Shimadzu Seisaku-sho Ltd. and marketed under product code of "DTG-40"), was found to be 25.2%. The determination of this ratio of decomposition was effected by heating a sample of the resinous particles (1) at a heating rate of 40° C./minute from the room temperature to 200° C., then continuing the heating at a gradually decreased heating rate so adjusted that the time required for the temperature to rise from the room temperature to 270° C. totalled 20 minutes, allowing the sample which had reached 270° C. to stand at that temperature for 40 minutes, and weighing the sample at the end of that period thereby finding the decrease in the weight of the sample due to the heating. For the determination, the sample size of the resinous particles was about 20 mg and clean air was supplied at a rate of 40 ml/minute to the site of the test.

Example 2

Resinous particles (2) were obtained by repeating the procedure of Example 1, except that 1 part of thiosalicylic acid was used instead of 1 part of the 3,4-dinitrobenzoic acid and the stirring with the T. K. Homogenizer was instead carried out at a rate of 6,000 r.p.m. for three minutes.

The solubility of thiosalicylic acid to water under the conditions of 23° C. and 760 Torrs was not more than 0.03% and the solubility to the polymeric monomer used was 1.6%.

The produced resinous particles (2) were tested for properties and the amount of minute particles by-produced by emulsion polymerization was determined in the same manner as in Example 1. The results are shown in Table 1.

Example 3

Resinous particles (3) were obtained by repeating the procedure of Example 1, except that 70 parts of butyl acrylate and 30 parts of styrene were instead used as polymeric monomer components and 5 parts of p-nitrobenzoic acid was used instead of 1 part of the 3,4-dinitrobenzoic acid.

The solubility of p-nitrobenzoic acid to water under the conditions of 23° C. and 760 Torrs was not more than 0.03% and the solubility to the polymeric monomer used was 0.48%.

The produced resinous particles (3) were tested for properties and the amount of minute particles by-produced by emulsion polymerization was determined in the same manner as in Example 1. The results are shown in Table 1.

Example 4

The same flask as used in Example 1 was charged with 900 parts of deionized water having dissolved therein 0.5 parts of polyoxyethylene alkyl sulfoammonium (produced by Dai-ichi Kogyo Seiyaku Co., Ltd. and marketed under trademark designation of "Hitenol N-08"). To the flask, a mixture prepared in advance of 75 parts of methyl methacrylate and 5 parts of ethylene glycol dimethacrylate as polymeric monomer components, 20 parts of titanium dioxide (produced by Ishihara Sangyo Kaisha Ltd. and marketed under trademark designation of "Tipaque CR-60-2") as a coloring agent, and 1 part of azoisobutyronitrile, and 1 part of thiosalicylic acid was added, then the resultant mixture was treated in the same manner as in Example 1 to give rise to resinous particles (4).

The solubility of thiosalicylic acid to the polymeric monomer used under the conditions of 23° C. and 760 Torrs was 1.6%.

The produced resinous particles (4) were tested for properties and the amount of minute particles by-produced by emulsion polymerization was determined in the same manner as in Example 1. The results are shown in Table 1.

Preliminary Synthesis Example 1

A flask provided with a stirrer, an inert gas inlet tube, a reflux condenser, and a thermometer was charged with 200 parts of deionized water having dissolved therein polyvinyl alcohol (produced by Kuraray Co., Ltd. and marketed under product code of "PVA-205"). To the flask, a mixture of 97 parts of styrene and 3 parts of glycidyl methacrylate as polymeric monomers and 8 parts of benzoyl peroxide was added then the resultant mixture was stirred at a high speed to give rise to a homogeneous suspension. Then, the suspension was blown with a forced current of nitrogen gas and, at the same time, heated to 80° C., then stirred at this temperature continuously for five hours to effect polymerization reaction, and cooled to obtain a polymer suspension. This polymer suspension was filtered, washed, and dried to obtain a polymer having an epoxy group as a reactive group.

By the use of a laboratory plastomill (produced by Toyo Seiki K.K.), 40 parts of the polymer having an epoxy group as a reactive group and 20 parts of carbon black (produced by Mitsubishi Chemical Industries, Ltd. and marketed under product code of "MA-100R") were kneaded to effect reaction under the conditions of 160° C. and 100 r.p.m., then cooled and pulverized to obtain a carbon black graft polymer (1). Example 5

The same flask as used in Example 1 was charged with 900 parts of deionized water having dissolved therein 0.5 part of polyoxyethylene alkyl sulfoammonium (produced by Dai-ichi Kogyo Seiyaku Co., Ltd. and marketed under trademark designation of "Hitenol N-08"). In the flask, the deionized water and a mixture prepared in advance of 76 parts of methyl methacrylate and 9 parts of trimethylol propane trimethacrylate as polymeric monomer components, 15 parts of the carbon black graft polymer (1) obtained as a coloring agent in Preliminary Synthesis Example 1, 1 part of azoisobutyronitrile, and 1 part of 2,2-dithiosalicylic acid were treated in the same manner as in Example 1 to obtain resinous particles (5).

The solubility of 2,2-dithiosalicylic acid to water under the conditions of 23° C. and 760 Torrs was not more than 0.03% and the solubility to the polymeric monomer used was not more than 0.03%.

The produced resinous particles (5) were tested for properties and the amount of minute particles by-produced by emulsion polymerization was determined in the same manner as in Example 1. The results are shown in Table 1.

Example 6

The same flask as used in Example 1 was charged with 900parts of deionized water having dissolved therein 0.5 part of polyoxyethylene nonylphenyl ether (produced by Sanyo Kasei K.K. and marketed under trademark designation of "Nonipol 200"). In the flask, the deionized water and a mixture prepared in advance of 80 parts of methyl methacrylate and 19 parts of ethylene glycol dimethacrylate as polymeric monomer components, 1 part of a fluorescent whiting agent (produced by Ciba Geigy and marketed under trademark designation of "Ubitex OB"), 0.5 parts of azoisobutyronitrile, and 2 parts of o-nitrobenzyl alcohol were treated in the same manner as in Example 1 to obtain resinous particles (6).

The solubility of o-nitrobenzyl alcohol to water under the conditions of 23° C. and 760 Torrs was 0.48% and the solubility to the polymeric monomer used was 23%.

The produced resinous particles (6) were tested for properties and the amount of minute particles by-produced by emulsion polymerization was determined in the same manner as in Example 1. The results are shown in Table 2.

Example 7

The same flask as used in Example 1 was charged with 900 parts of deionized water having dissolved therein 0.5 parts of polyvinyl alcohol (produced by Kuraray Co., Ltd. and marketed under product code of "PVA-205"). In the flask, the deionized water and a mixture prepared in advance of 70 parts of methyl methacrylate and 9 parts of trimethylol propane trimethacrylate as polymeric monomer components, 20 parts of titanium dioxide (produced by Ishihara Sangyo Kaisha, Ltd. and marketed under trademark designation of "Tipaque CR-60-2") as a coloring agent, 1 part of a fluorescent whiting agent (produced by Ciba Geigy and marketed under trademark designation of "Ubitex OB"), 1 part of azoisobutyronitrile, and 1 part of thiosalicylic acid were treated in the same manner as in Example 1 to obtain resinous particles (7).

The solubility of thiosalicylic acid in the polymeric monomers used under the conditions of 23° C. and 760 Torrs was 1.6%.

The produced resinous particles (7) were tested for properties and the amount of minute particles by-produced by emulsion polymerization was determined in the same manner as in Example 1. The results are shown in Table 2.

Control 1

The same flask as used in Example 1 was charged with 900 parts of deionized water having dissolved therein 0.5 parts of polyvinyl alcohol (produced by Kuraray Co., Ltd. and marketed under product code "PVA-205"). In the flask, the deionized water and a mixture prepared in advance of 90 parts of methyl methacrylate, 10 parts of ethylene glycol dimethacrylate, and 1 part of azoisobutyronitrile were stirred using a T. K. Homogenizer (produced by Tokushu Kika Kogyo K.K.) at 6,000 r.p.m. for three minutes to obtain resinous particles (C1) for comparison.

The produced resinous particles (C1) for comparison were tested for properties and the amount of minute particles by-produced by emulsion polymerization was determined in the same manner as in Example 1. The results are shown in Table 2.

Control 2

The same flask as used in Example 1 was charged with 900 parts of deionized water having dissolved therein 0.5 part of polyoxyethylene alkyl sulfoammonium (produced by Dai-ichi Kogyo Seiyaku Co., Ltd. and marketed under trademark designation of "Hitenol N-08"). When the deionized water and a mixture prepared in advance of 90 parts of methyl methacrylate, 10 parts of trimethylol propane trimethacrylate, and 1 part of azoisobutyronitrile were treated in the same manner as in Example 1, the suspension in the process of polymerization suffered from poor stability of dispersion and the greater part of the nonvolatile component aggregated and settled to the bottom of the flask.

Control 3

The same flask as used in Example 1 was charged with 900 parts of deionized water having dissolved therein 0.5 part of polyoxyethylene alkyl sulfoammonium (produced by Dai-Ichi Kogyo Seiyaku Co., Ltd. and marketed under trademark designation of "Hitenol N-08") and 1 part of cupric chloride. When the deionized water and a mixture prepared in advance of 90 parts of methyl methacrylate, 10 parts of trimethylol propane trimethacrylate, and 1 part of azoisobutyronitrile were treated in the same manner as in Example 1, the suspension in the process of polymerization suffered from poor stability of dispersion and the greater part of the nonvolatile component aggregated and settled to the bottom of the flask.

Control 4

The same flask as used in Example 1 was charged with 900 parts of deionized water having dissolved therein 0.5 part of polyoxyethylene alkyl sulfoammonium (produced by Dai-ichi Kogyo Seiyaku Co., Ltd. and marketed under trademark designation of "Hitenol N-08") and 1 part of thioglycolic acid. In the flask, the deionized water and a mixture prepared in advance of 90 parts of methyl methacrylate, 10 parts of trimethylol propane trimethacrylate, and 1 part of azoisobutyronitrile were treated in the same manner as in Example 1 to obtain resinous particles (C4) for comparison.

The produced resinous particles (C4) for comparison were tested for properties and the amount of minute particles by-produced by emulsion polymerization was determined in the same manner as in Example 1. The results are shown in Table 3.

Control 5

When the procedure of Example 1 was repeated except that 1 part of dodecyl mercaptan (soluble in any desired proportion in methyl methacrylate and trimethylol propane trimethacrylate as polymeric monomer components) was used instead of 1 part of the 3,4-dinitorobenzoic acid, the polymerization reaction was retarded and the greater part of the volatile component aggregated and settled to the bottom of the flask.

TABLE 1

| No. | Example 1 | Example 2 | Example 3 | Example 4 | Example 5 |
|---|---|---|---|---|---|
| Resinous particle | (1) | (2) | (3) | (4) | (5) |
| Polymeric monomer (A) | | | | | |
| Methyl methacrylate | 90 | 90 | — | 75 | 76 |
| Butyl acrylate | — | — | 70 | — | — |
| Styrene | — | — | 30 | — | — |
| Trimethylolpropane trimethacrylate | 10 | 10 | — | — | 9 |
| Etylene glycol dimethacrylate | — | — | — | 5 | — |
| Compound (B) | | | | | |
| Type | 3,4-dinitrobenzoic acid | thiosalicylic acid | p-nitrobenzoic acid | thiosalicylic acid | 2,2-ditiosalicylic acid |
| Amount | 1 | 1 | 5 | 1 | 1 |
| Emulsifying agent | | | | | |
| Type | Hitenol N-08 | ← | ← | ← | ← |
| Amount | 0.5 | ← | ← | ← | ← |
| Other Additive | — | — | — | Titanium dioxide 20 | Carbon black graft polymer (1) 15 |
| Properties of particles | | | | | |
| Particle diameter (μm) | 3.47 | 10.5 | 4.09 | 2.72 | 4.18 |
| Particle diameter distribution (μm) | 1.4 | 3.1 | 1.8 | 1.2 | 1.7 |
| Color | Colorless | Colorless | Colorless | White | Black |
| Odor | Odorless | Odorless | Odorless | Odorless | Odorless |
| Refractive index | 1.49 | 1.49 | 1.53 | — | — |
| Decomosiption ratio of organic component (%) | 25.2 | 13.5 | 13.5 | 10.7 | 20.5 |
| Amount of emulsion polymerized polymer (g) | 1.48 | 0.27 | 0.27 | 0.41 | 1.46 |

TABLE 2

| No. | Example 6 | Example 7 | Control 1 | Control 2 | Control 3 |
|---|---|---|---|---|---|
| Resinous particle | (6) | (7) | (C1) | | |
| Polymeric monomer (A) | | | | | |
| Methyl methacrylate | 80 | 70 | 90 | 90 | 90 |
| Butyl acrylate | — | — | — | — | — |
| Styrene | — | — | — | — | — |
| Trimethylolpropane trimethacrylate | — | 9 | — | 10 | 10 |

TABLE 2-continued

| No. | Example 6 | Example 7 | Control 1 | Control 2 | Control 3 |
|---|---|---|---|---|---|
| Etylene glycol dimethacrylate | 19 | — | 10 | — | — |
| Compound (B) | | | | | |
| Type | 0-nitrobenzyl alcohol | thiosalicylic acid | — | — | — |
| Amount | 2 | 1 | — | — | — |
| Emulsifying agent | | | | | |
| Type | Nonipol 200 | PVA-205 | ← | Hitenol N-08 | ← |
| Amount | 0.5 | 0.5 | ← | 0.5 | ← |
| Other Additive | Fluorescent whitening agent 1 | Titanium dioxide 20 Fluorescent whitening agent 1 | — | — | Cupric chloride 1 |
| Properties of particles | | | | | |
| Particle diameter ($\mu$m) | 3.52 | 2.33 | 12.5 | The greater part of the nonvolatile component aggregated in the process of suspension polymerization. | The greater part of the nonvolatile component aggregated in the process of suspension polymerization. |
| Particle diameter distribution ($\mu$m) | 1.3 | 0.8 | 3.7 | | |
| Color | Colorless (Fluoresced) | White (Fluoresced) | Colorless | | |
| Odor | Odorless | Odorless | Odorless | | |
| Refractive index | 1.50 | — | 1.49 | | |
| Decomposition ratio of organic component (%) | 12.5 | 9.5 | 98.5 | | |
| Amount of emulsion polymerized polymer (g) | 1.52 | 0.21 | 25.6 | | |

TABLE 3

| No. | Control 4 | Control 5 |
|---|---|---|
| Resinous particle | (C4) | |
| Polymeric monomer (A) | | |
| Methyl methacrylate | 90 | 90 |
| Butyl acrylate | — | — |
| Styrene | — | — |
| Trimethylolpropane trimethacrylate | 10 | 10 |
| Etylene glycol dimethaerylate | — | — |
| Compound (B) | | |
| Type | — | — |
| Amount | — | — |
| Emulsifying agent | | |
| Type | Hitenol N-08 | ← |
| Amount | 0.5 | ← |
| Other Additive | Tioglycolic acid 1 | Dodecyl mercaptan 1 |
| Properties of particles | | |
| Particle diameter ($\mu$m) | 2.45 | The greater part of the nonvolatile component aggregated in the process of suspension polymerization. |
| Particle diameter distribution ($\mu$m) | 1.1 | |
| Color | Colorless | |
| Odor | Specific odor | |
| Refractive index | 1.49 | |
| Decomposition ratio of organic component (%) | 95.2 | |
| Amount of emulsion polymerizated polymer (g) | 1.27 | |

Example 8

In a Banbury mixer, 99 parts of polypropylene (melt flow index (MI) 2 g/10 minutes and heptane soluble content 3%) and 1 part of the resinous particles (1) obtained in Example 1 were kneaded and pelletized at 230° C. to obtain colorless pellets (1). Then, a stretched polypropylene film (1) was obtained by mixing 10 parts of the pellets and 90 parts of the same polypropylene as mentioned above, extruding the resultant mixture in the form of a sheet through an extruding device at 260° C., stretching the extruded sheet to 5 times the original size longitudinally and 9 times the original side laterally under the conditions of 140° C. of stretching temperature in the longitudinal direction and 175° C. of stretching temperature in the lateral direction, and subjecting one surface of the stretching film to a treatment with corona discharge.

The stretched polypropylene film (1) obtained as described above was tested for thickness, turbidity, coefficient of kinetic friction, blocking strength, and modulus of tensile elasticity. The results are shown in Table 4. The blocking strength and the coefficient of kinetic friction were severally determined of both the surface of the film subjected to the treatment with corona discharge and the surface thereof not subjected to the treatment.

The turbidity, coefficient of kinetic friction, blocking strength, and modulus of tensile elasticity of the film were analyzed and evaluated by the following methods.

Turbidity

This property was determined in accordance with Japanese Industrial Standard (JIS) K 6714 using a turbidimeter (produced by Nippon Denshoku Kogyo K.K. and marketed under trademark designation of "Colorimeter NDH-1001DP").

Modulus of kinetic friction

This property was determined by preparing two sample films 50 mm in width, superposing them, placing the superposed sample films under a load of 200 g, causing one of the superposed sample films to slide on the other sample film at a friction speed of 35 mm/min, measuring the value of resistance (g) consequently generated between the two sample films, and calculating the coefficient in accordance with the following formula. The determination of this value of resistance was effected using a slide testing device made by Toyo Seiki K.K.

Coefficient of kinetic friction=(Scale reading of chart (g))/(200 g)

Blocking strength (g/cm$^2$)

This property was determined by preparing two sample films measuring 120 mm×120 mm, superposing the two sample films, allowing the superposed sample films to stand under a load of 73 g/cm$^2$ in an atmosphere kept at 40° C. and 90% RH for 24 hours, cutting from the superposed sample films a part having a blocking area of 12 cm$^2$, measuring shear peel strength (g) of the part using an autograph, and calculating the blocking strength by the following formula.

Blocking strength=(Shear peel strength (g))/(12cm$^2$)

Modulus of tensile elasticity (kg/mm$^2$)

This property was determined in accordance with ASTM D-883, with necessary modifications.

Preliminary Synthesis Example 2

In a four-neck flask provided with a stirrer, a reflux condenser, and a thermometer, 150 parts of benzoguanamine, 130 parts of 37% formalin, and 0.52 parts of an aqueous 10% sodium carbonate solution were mixed. The mixture, with the pH thereof adjusted to 8.0, was stirred and at the same time heated to 95° C. and left reacting for four hours to obtain a soluble and fusible resin.

Separately, 8 parts of polyvinyl alcohol (produced by Kuraray Co., Ltd. and marketed under product code of "PVA-205") was dissolved in 750 parts of water. This aqueous solution was heated to 90° C. and stirred using a homomixer (produced by Tokushu Kika Kogyo K.K.). A white emulsion was produced by throwing the soluble and fusible resin into the aqueous solution kept in the stirred state. A suspension of minute hardened resinous particles was obtained by cooling the emulsion to 40° C., adding 2 parts of dodecyl benzene sulfonic acid to the cooled emulsion, gently stirring the resultant mixture with an anchor type stirring device and simultaneously keeping the stirred mixture at 40° C. for two hours, and stirring and hardening the mixture for two hours each at 50° C., 60° C., and 90° C. Resinous particles (C6) for comparison were obtained by filtering the suspension and drying the particles stopped on the filter.

The resinous particles (C6) for comparison thus obtained were found to have an average particle diameter of 3.32 μm and a size distribution of 1.6 μm.

Control 6

In a Banbury mixer, 99 parts of the same polypropylene as used in Example 8 and 1 part of the resinous particles (C6) for comparison obtained in Preliminary Synthesis Example 2 were kneaded and pelletized at 230° C. to obtain light yellow pellets (C1) for comparison. Then a stretched polypropylene film (C1) for comparison was obtained by mixing 10 parts of the pellets (C1) for comparison with 90 parts of the aforementioned polypropylene, extruding the resultant mixture in the form of a sheet through an extruding device at 260° C., stretching the extruded sheet to 5 times the original side longitudinally and 9 times the original size laterally under the conditions of 140° C. of stretching temperature in the longitudinal direction and 175° C. of stretching temperature in the lateral direction, and subjecting one surface of the stretched film to a treatment with corona discharge.

The stretched polypropylene film (C1) for comparison obtained as described above was tested for thickness, turbidity, coefficient of kinetic friction, blocking strength, and modulus of tensile elasticity in the same manner as in Example 8. The results are shown in Table 4.

Example 9

In a Banbury mixer, 75 parts of low-density polyethylene (melt flow index (MI) 2.0 g/10 minutes and density 0.92 g/cm$^3$) and 25 parts of the resinous particles (2) obtained in Example 2 were kneaded and pelletized at 220° C. to obtain colorless pellets (2). Then, a polyethylene film (1) was obtained by mixing 2 parts of the pellets (2) with 98 parts of the same low-density polyethylene as described above and extruding the resultant mixture in the form of a sheet through a T die of an extruding device at 200° C.

The polyethylene film (1) obtained as described above was tested for thickness, turbidity, coefficient of kinetic friction, blocking strength, and coefficient of tensile elasticity. The results are shown in Table 4.

Control 7

In a Banbury mixer, 75 parts of the same low-density polyethylene as used in Example 9 and 25 parts of the resinous particles (C1) for comparison obtained in Control 1 were kneaded and pelletized at 220° C. to obtain light yellow pellets (C2) for comparison. Then, a polyethylene film (C1) for comparison was obtained by mixing 2 parts of the pellets (C2) for comparison with 98 parts of the same low-density polyethylene as mentioned above and extruding the resultant mixture in the form of a sheet through a T die of an extruding device at 200° C.

The polyethylene film (C1) for comparison obtained as described above was tested for thickness, turbidity, modulus of kinetic friction, blocking strength, and modulus of tensile elasticity in the same manner as in Example 8. The results are shown in Table 4.

TABLE 4

| No. | Example 8 | Control 6 | Example 9 | Control 7 |
| --- | --- | --- | --- | --- |
|  | Stretched polypropylene film (1) | Stretched polypropylene film (C1) | Polyethylene film (1) | Polyethylene film (C1) |
| Polyolefin | Polypropylene | ← | Low-density polyethylene | ← |
| Resinous particle | (1) | (C6) | (2) | (C1) |
| Blended amount of resinous particle | 0.1 | 0.1 | 0.5 | 0.5 |

TABLE 4-continued

| No. | Example 8 | Control 6 | Example 9 | Control 7 |
| --- | --- | --- | --- | --- |
| (% by weight) | | | | |
| Stretching magnification | | | | |
| Longitudinal | 5 | 5 | — | — |
| Laternal | 9 | 9 | — | — |
| Thickness ($\mu$m) | 20 | 20 | 50 | 50 |
| Turbidity (%) | 1.0 | 3.5 | 5.3 | 10.4 |
| Kinetic friction coefficient | | | | |
| Treated surface | 0.15 | 0.33 | 0.24 | 0.27 |
| Untreated surface | 0.18 | 0.34 | 0.25 | 0.30 |
| Blocking strength (g/cm$^2$) | | | | |
| Treated surface | <10 | 15 | <10 | <10 |
| Untreated surface | <10 | <10 | <10 | <10 |
| Modulus of tensile elasticity (kg/mm$^2$) | | | | |
| Longitudinal | 186 | 143 | 14 | 9 |
| Laternal | 337 | 303 | 16 | 10 |
| Odor at film forming | No | Yes | No | No |

Example 10 and Control 8

A coating composition (1) and a coating composition (C1) for comparison were obtained by dissolving an acryl type polymer (produced by Mitsubishi Rayon Company Limited and marketed under trademark designation of "Dianar BR-112") in a 50/50 ethyl acetate/-toluene solution, adding the resinous particles (1) obtained in Example 1 and polymethyl sesquioxane particles having an average particle diameter of 3.0 $\mu$m (produced by Toshiba Silicone K.K. and marketed under trademark designation of "Tospearl 130") in amounts indicated in Table 5 to the resultant solution, and thoroughly stirring the resultant mixtures.

An undercoating agent prepared by mixing 10 parts of a polyester type polymer (a 50% solution in ethyl acetate, produced by Toyo Morton K.K. and marketed under product code of "AD1010") with 1 part of polyisocyanate (a 75% solution in ethyl acetate, produced by Toyo Morton K.K. and marketed under product code of "Cat 10") and diluting the resultant mixture with ethyl acetate was applied to a stretched polypropylene film and dried thereon. On the undercoated stretched polypropylene film, the coating compositions mentioned above were each applied and dried to form a coating layer 1.7 $\mu$m in thickness and give rise to a coated film. The coated films consequently obtained were tested for coefficient of kinetic friction, blocking strength, and resistance to scratching. The results are shown in Table 5.

TABLE 5

| No. | Example 10 | Control 2 |
| --- | --- | --- |
| Coating composition | (1) | (C1) |
| Components of coating composition (part) | | |
| Resinous particle (1) | 0.3 | — |
| Tospearl 130 | — | 0.3 |
| Dianar BR-113 | 19.7 | 19.7 |
| Ethyl acetate | 40 | 40 |
| Toluene | 40 | 40 |
| Capability of coated film | | |
| Kinetic friction coefficient | 0.13 | 0.15 |
| Blocking strength (g/cm$^2$) | <10 | <10 |
| Resistance to scratching*[1] | ○ | X |

*[1]Determination of resistance to scratching:

This property was determined by preparing two sample films measuring 10 cm × 10 cm, contacting a coated surface of one film to an uncoated surface of another film, scratching the surfaces of each other by moving a 5 kg load in a reciprocating motion 5 times across the contacted films and, then visually examining the uncoated surface as to the extent of scratching.

It is clearly noted from the data of Table 5 that the coating composition of this invention excelled in the resistance to scratching.

Example 11 and Control 9

A coating composition (2) and a coating composition (C2) for comparison were obtained by dissolving vinyl chloride-vinyl acetate copolymer (produced by Nippon Bion K.K. and marketed under product code of "400K-110A"), polyurethane (produced by Nippon Polyurethane K.K. and marketed under trademark designation of "Nippolan 2301"), and polyisocyanate (produced by Nippon Polyurethane K.K. and marketed under trademark designation of "Coronate L") as binders in proportions indicated in Table 6 in methylethyl ketone, adding the resinous particles (5) obtained in Example 5 and carbon black (produced by Asahi Carbon K.K. and marketed under trademark designation of "Asahi #60") in amounts indicated in Table 6 to the resultant solutions, and severally stirring the resultant mixtures thoroughly. The coating composition (2) and the coating composition (C2) for comparison were tested for antistatic property, coefficient of friction, wear resistance, and delustering property. The results are shown in Table 6.

TABLE 6

| No. | Example 11 | Control 9 |
| --- | --- | --- |
| Coating composition | (2) | (C2) |
| Components of coating composition (part) | | |
| Resinous particle (5) | 60 | — |
| Carbon black (Asahi #60) | — | 30 |
| 400X-110A | 17 | 30 |
| Nippolan 2301 | 9 | 15 |
| Coronate L | 14 | 25 |
| Methylethyl ketone | 300 | 300 |
| Capability of coated film | | |
| Antistatic property | 1.7 × 10$^4$ | 8.5 × 10$^4$ |
| Friction coefficient | 0.21 | 0.34 |
| Wear resistance | ○ | X |
| Delustering property | ○ | X |

It is clearly noted from the data of Table 6 that the coating composition of the present invention exhibited ideal dispersibility and excelled in antistatic property, slip property, wear resistance, and delustering property.

The properties indicated in Table 6 were tested by the following methods.

Antistatic property:

This property was determined by holding a sample in an atmosphere kept at 25° C. and 60% RH for 24 hours and measuring the surface electric resistance of the sample after the standing.

Coefficient of friction:

This property was determined by using stainless steel balls and measuring the coefficient of kinetic friction μ (at 3.3 cm/sec) genarated by the ball with the sample surface.

Wear resistance:

This property was determined by giving 100 reciprocations to a sample held in place in a Gakushin type dye fastness tester in accordance with JIS L-1084 45R, and visually examining the sample as to the extent of wear consequently produced. The abrasion wear was rated on the two-point scale, wherein O stands for absence of wear and X for presence of wear.

Delustering property:

This property was determined by visual examination on the two-point scale, wherein O stands for satisfactory delustering property and X for inferior delustering property.

Example 12 and Control 10

In a Henschel mixer, zinc white, mica, talc, and iron oxide were mixed with the resinous particles (4) obtained in Example 4 or with titanium dioxide in amounts indicated in Table 7 to obtain a mixed powder. Separately, liquid paraffin, sorbitan sesquioleate, ethyl paraben, vitamin E, and perfume were heated and dissolved in amounts indicated in Table 7 at 80° C. The resultant solution was sprayed onto the mixed powder and they were continuously mixed in the Henschel mixer. The produced mixture was pulverized by the use of an atomizer, sifted, and compression molded in a plate. Thus, a cosmetic article (1) and a cosmetic article (C1) for comparison were obtained.

These cosmetic articles were subjected to an organoleptic examination conducted by a panel of ten members. The results are shown in Table 7.

TABLE 7

| No. | Example 12 | Control 10 |
| --- | --- | --- |
| Cosmetic article | (1) | (C1) |
| Composition of cosmetic article (part) | | |
| Resinous particle (4) | 20.0 | — |
| Titanium dioxide | — | 10.0 |
| Zinc white | 13.0 | 15.0 |
| Mica | 34.66 | 40.0 |
| Talc | 13.42 | 15.48 |
| Iron oxide | 3.9 | 4.5 |
| Liquid paraffin | 13.0 | 13.0 |
| Sorbitan sesquioleate | 1.0 | 1.0 |
| Ethylparaben | 0.5 | 0.5 |
| Vitamin E | 0.02 | 0.02 |
| Perfume | 0.5 | 0.5 |
| Users' feeling | | |
| Adhesion to the skin | O | X |
| Fastness of adhesion to the skin | O | Δ |
| Covering capacity | O | Δ |
| Retention of makeup | O | Δ |

It is clearly noted from the data of Table 7 that the cosmetic article of this invention was excellent in the sensation of intimate adhesion to the skin, fastness of adhesion to the skin, covering capacity, and retention of makeup.

The marks of the three-point scale used in rating the items of examination shown in Table 7 have the following meanings: O for 8 to 10 members of the panel, Δ for 5 to 7 members of the panel, and X for 0 to 4 members of the panel, respectively finding the relevant sample satisfactory for use.

What is claimed is:

1. A method for the production of resinous particles, which comprises suspending a polymerizable monomer (A) containing a (meth)acrylic monomer as a main component in an aqueous medium and polymerizing said polymerizable monomer (A) in the presence of a compound (B) which is at least of one compound selected from the group consisting of 3,4-dinitrobenzoic acid, thiosalicylic acid, nitrobenzoic acid, dithiosalicylic acid and nitrobenzyl alcohol.

2. A method according to claim 1, wherein the amount of said compound (B) to be added is in the range of 20 to 0.0001% by weight, based on the amount of said polymerizable monomer (A).

3. A method according to claim 1, wherein the polymerization is carried out in the presence of at least one additive selected from the group consisting of plasticizer, polymerization stabilizer, coloring agent, fluorescent whiting agent, magnetic powder, ultraviolet absorbent, anti-static agent, and flame retardant.

* * * * *